United States Patent [19]

Zaar

[11] 4,214,108
[45] Jul. 22, 1980

[54] 1,5,9-CYCLODODECATRIENE FROM BUTADIENE TRIMERIZATION USING DIBENZYLBENZENES

[75] Inventor: Wolfgang Zaar, Marl, Fed. Rep. of Germany

[73] Assignee: Chemische Werke Hüls Aktiengesellschaft, Marl, Fed. Rep. of Germany

[21] Appl. No.: 45,287

[22] Filed: Jun. 4, 1979

[30] Foreign Application Priority Data

Jun. 9, 1978 [DE] Fed. Rep. of Germany ....... 2825341

[51] Int. Cl.² .......................... C07C 3/60; C07C 13/02
[52] U.S. Cl. ...................................... 585/23; 585/366; 585/369; 585/370
[58] Field of Search .................. 585/23, 366, 369, 370

[56] References Cited

U.S. PATENT DOCUMENTS

| | | | |
|---|---|---|---|
| 2,954,412 | 9/1960 | Wulf et al. | 585/422 |
| 2,964,574 | 12/1960 | Wilke | 585/23 |
| 3,223,741 | 12/1965 | Feldman et al. | 585/370 |
| 3,424,774 | 1/1969 | Tornquist | 585/23 |

Primary Examiner—Veronica O'Keefe
Attorney, Agent, or Firm—Gibert L. Wells

[57] ABSTRACT

The process for making cyclododecatriene(1,5,9)-enes by catalytically trimerizing butadiene using a catalyst from a titanium halide and an alkylaluminum halide in the presence of hydrocarbons or halogenated hydrocarbons is improved by carrying out the reaction in the presence of dibenzyenes having the general formula

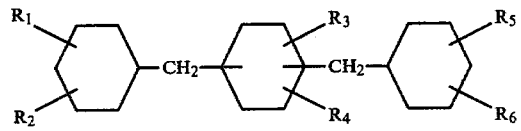

where $R_1$ through $R_6$ represent hydrogen atoms, halogen atoms, alkyl groups, aralkyl groups, cycloalkyl groups, or aryl groups, the dibenzylbenzenes being used in at least equimolar amounts with respect to the titanium compound.

6 Claims, No Drawings

1,5,9-CYCLODODECATRIENE FROM BUTADIENE TRIMERIZATION USING DIBENZYLBENZENES

CROSS-REFERENCE TO RELATED APPLICATION

Applicant claims priority under 35 USC 119 for application No. P 28 25 341.0, filed June 9, 1978 in the Patent Office of the Federal Republic of Germany.

BACKGROUND OF THE INVENTION

The field of the invention is hydrocarbons and the present invention is particularly concerned with the preparation of cyclododecatri-(1,5,9)-enes by catalytically trimerizing butadiene using a catalyst of a titanium halide and an alkyl aluminum halide in the presence of hydrocarbons or halogenated hydrocarbons.

The state of the art of catalytic trimerization of butadienes to cyclododecatrienes may be ascertained by reference to U.S. Pat. No. 2,964,574 and German Pat. No. 1,112,069, the disclosures of which are incorporated herein.

The cyclododecatri-(1,5,9)-enes are recovered by distillation and vinylcyclohexene and cyclooctadi-(1,5)-ene are obtained as distilled by-products and higher butadiene polymers as non-distilled by-products. The polymers initially dissolved in the mixture of reaction cause an appreciable increase in the viscosity of the solution and thereby the butadiene absorption is decreased and difficult processing of the mixture of the reaction occurs. The process is also known to work in the presence of complexing additives or semi-polar compounds and in the presence of slight amounts of water, for the purpose of decreasing the formation of higher polymers as disclosed in U.S. Pat. Nos. 3,076,045 and 3,149,173 and British Pat. No. 1,102,833, the disclosures of which are incorporated herein.

Dibenzylbenzenes useful in the present invention are disclosed in U.S. Pat. No. 2,954,412, the disclosure of which is incorporated herein.

Hydrocarbons or halogenated hydrocarbons such as benzene, toluene, xylene, chlorobenzene, heptane, cyclohexane, isooctane, even cyclododecatriene itself, especially however, benzene, are used as diluents in the trimerization. These low-boiling point diluents after completion of reaction are first distilled off and only then, and in another distillation batch, follows the higher-boiling-point cyclododecatriene and the other oligomers, vinylcyclohexene and cyclooctadiene. The catalyst remains in the residue and therefore cannot be used again in the next batch or in a continuous process on account of the required recovery.

SUMMARY OF THE INVENTION

Having in mind the limitations of the prior art, the objects of the present invention are to process cyclododecatri-(1,5,9)-enes so that butadiene absorption is improved, the catalytic activity is increased, the reaction is continuous and the recovery is improved.

These objects are achieved by carrying out the trimerization in the presence of dibenzylbenzenes having the general formula

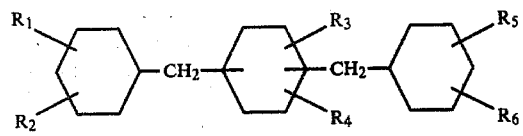

where $R_1$ through $R_6$ represent hydrogen or halogen atoms, alkyl groups, aralkyl groups, cycloalkyl groups or aryl groups, the dibenzylbenzenes being used in at least equimolar quantities with respect to the titanium compound.

Specific examples of the general formula include o-dibenzylbenzene, p-dibenzylbenzene, 1-methyl-2,6-dibenzylbenzene, 1-methyl-2,5-dibenzylbenzene, 1-methyl-3,5-dibenzylbenzene, 1-methyl-2,4-dibenzylbenzene, 1,4-dimethyl-2,5-dibenzylbenzene, 1 p-tolyl-3,5-dibenzylbenzene, 1-chloro-2,6-dibenzylbenzene, 1-benzyl-3,5-di-p-cyclohexylbenzylbenzene.

DESCRIPTION OF THE PREFERRED EMBODIMENTS

The dibenzylbenzenes can be obtained using the process described in U.S. Pat. No. 2,954,412. As a rule, the dibenzylbenzenes are mixtures of isomers and generally their boiling points exceed 380° C. Advantageously, the so-called dibenzyltoluene with a boiling point of about 390° C. at normal pressure is used. The dibenzylbenzenes can be used together with the prior art diluents. However, they can also be used as the sole diluent. Despite the higher viscosity, the catalytic effectiveness when compared to the conventional diluents of low boiling points such as benzene, toluene or xylene does not decrease, rather the absorption of butadiene is increased. Because the catalytic effectiveness is increased, an improved yield in cyclododecatriene is obtained. Accordingly, the dibenzylbenzenes not only represent diluents, they are effective moderators in addition. When the dibenzylbenzenes are used alone, the process furthermore offers the advantage that the low boiling-point cyclododecatrienes can be separated by distillation from the mixture of reaction without having to remove the low boiling-point solvents beforehand. Following separation by distillation, or substantial distillation of the desired products of reaction, vinylcyclohexene, cyclooctadiene and cyclododecatriene—which takes place under reduced pressure at temperatures up to 150° C.—the mixture of catalysts remaining in the residue, and preliminarily exhausted, can be used again with almost full activity. Accordingly, the process may be continuous in form by feeding back the catalyst, where appropriate after replenishing the catalyst, into the reaction. This feedback is possible because the catalyst in the process of the present invention precipitates not as a heterogeneous suspension as is the case of the prior art diluents, rather it precipitates homogeneously, that is, without solid bodies detectable by the naked eye. When the mixture containing the catalyst becomes excessively viscous due to dissolved polymer components, dilution can be obtained prior to feedback by adding further solvent, or the high-molecular components are separated by distilling the solvent.

When a mixture of dibenzylbenzenes and benzene is used, the benzene together with the cyclododecatrienes are easily separated by steam distillation. The cyclododecatrienes so obtained contain less than 1% of by-products and are suitable without further purifying operations for most subsequent reactions.

The dibenzylbenzenes are used in at least equimolar amounts with respect to the titanium compound being used. The upper limit depends on the particular application, that is, excessive dilution should be avoided, so that excessive amounts of solvents need not be stirred into the reaction mixture. A useful range of molar ratios of titanium compound: dibenzylbenzenes is about 1:1 to 1:10,000, advantageously 1:200 to 1:3,000.

Trimerization is carried out at the conventional temperatures below 150° C., advantageously between about 20° and 100° C., especially between 40° and 80° C.

The known catalysts of titanium tetrachloride and alkylaluminum chloride or of titanium trichloride or titanium dichloride and dialkylaluminum chloride or alkylaluminum dichloride or alkylaluminum sesquichloride are useful. Advantageously, ethylaluminum sesquichloride is used. The atomic ratio of aluminum:titanium is the conventional range from 2:1 to 140:1; a ratio of 50:1 to 70:1 being advantageous and titanium tetrachloride is used in concentrations from 0.25 to 5.7 millimoles per liter of solvent.

The preparation of the catalyst takes place in conventional manner by first dissolving the alkylaluminum halide in the solvent used (dibenzylene and where appropriate for instance benzene), and by subsequently adding the titanium halide. This catalyst preparation ordinarily takes place at temperatures between 40° and 70° C. The solvents used contain the ordinary amounts of water from 100 ppm to 400 ppm and this corresponds to an amount of 0.1 to 0.4 moles per mole of aluminum compound. After the conventional aging time has elapsed, butadiene is introduced into the solution containing the catalyst.

The following specific examples further illustrate the present invention.

COMPARISON EXAMPLE 1 (V1)

First, 27 millimoles of ethylaluminum sesquichloride are dissolved in 238 g of benzene with a water content of 115 ppm and under an atmosphere of nitrogen. In the course of 15 minutes and at a temperature of 70° C., 4.5 millimoles of titanium tetrachloride dissolved in 202 g of benzene are then added. Following further stirring, butadiene is introduced after 15 minutes. 474 g of butadiene are absorbed in the course of one hour. The products are then separated by steam distillation. After distillation, 400 g of cyclododecatriene, 7.8 g of vinylcyclohexene and 4.2 g of cyclooctadiene are obtained for a 96% conversion.

COMPARISON EXAMPLE 2 (V2)

Other conditions being the same, 430 g of toluene are used in lieu of 440 g of benzene. 590 g of butadiene are absorbed. After distillation, 490 g of cyclododecatriene, 12.6 g of vinylcyclohexene and 6.0 g of cyclooctadiene are obtained for a 97% conversion.

EXAMPLE 1 (B1)

Other conditions being the same, a mixture of 430 g of benzene and 12.2 g of dibenzylbenzene is used in lieu of 440 g of benzene or 430 g of toluene. 680 g of butadiene are absorbed. After distillation 619 g of cyclododecatriene, 10.5 g of vinylcyclohexene and 6.6 g of cyclooctadiene are obtained for a 97% conversion.

EXAMPLE 2 (B2)

502 g of dibenzyltoluene are used as the single solvent. 983 g of butadiene are absorbed. After distillation 937 g of cyclododecatriene, 7.5 g of vinylcyclohexene and 9.9 g of cyclooctadiene are obtained for a 97% conversion.

The results from Comparison Examples 1 and 2 and of Examples 1 and 2 are contrasted in the table below. The improved yield in cyclododecatriene and the improved catalytic activity is readily apparent where VCH means vinylcyclohexene, COD means cyclooctadiene and CDT means cyclododecatriene.

Table 1

| Ex. | $Et_3Al_2Cl_3$ mMoles | $TiCl_4$ mMoles | Kind of solvent | Di-benzyl-toluene g | Temperature °C. | Reaction time h | Butadiene abs. g |
|---|---|---|---|---|---|---|---|
| V1 | 27 | 4.5 | Benzene 440 | — | 70–75 | 1 | 474 |
| V2 | 27 | 4.5 | Toluene 430 | — | 70–75 | 1 | 590 |
| B1 | 27 | 4.5 | Benzene 430 | 12.2 | 70–75 | 1 | 680 |
| B2 | 27 | 4.5 | — | 502 | 70–75 | 1 | 983 |

| Ex. | Conversion % | Product Distribution VCH g | COD g | CDT g | Residue (>$C_{12}$) g | Catalyst Activity g Product / mMoles Ti · h |
|---|---|---|---|---|---|---|
| V1 | 96 | 7.8 | 4.2 | 400 | 48.0 | 102 |
| V2 | 97 | 12.6 | 6.0 | 490 | 63.0 | 127 |
| B1 | 97 | 10.5 | 6.6 | 619 | 22.4 | 146 |
| B2 | 97 | 7.5 | 9.9 | 937 | 10.1 | 214 |

EXAMPLES 3–6

520 g of dibenzyltoluene are used as the sole solvent again at a temperature between 70 and 75° C. The amount of catalyst was 2.25 mMoles of $TiCl_4$ and 13.5 mMoles of ethylaluminum sesquichloride. Table 2 shows the results for various times of reaction in summary form.

Table 2

| Example | Reaction Time | Butadiene absorption g | Conversion % | VCH g | COD g | CDT g | Residue g | Activity g Product / mMoles Ti · h |
|---|---|---|---|---|---|---|---|---|
| 3 | 30 | 155 | 88.2 | 5.6 | — | 132.0 | — | 122.3 |
| 4 | 90 | 765 | 93.3 | 12.0 | 7.1 | 668.0 | 30.0 | 212.5 |
| 5 | 190 | 1430 | 95.5 | 34.0 | 25.2 | 1251.0 | 62.0 | 194.0 |
| 6 | 300 | 1820 | 93.8 | 34.0 | 38.3 | 1556.0 | 84.2 | 152.2 |

EXAMPLE 7

Dibenzyltoluene is used as the sole diluent. Upon completion of the reaction, that is, as the absorption of butadiene slackens, the catalyst is not destroyed, rather the oligomer mixture of cyclododecatriene, vinylcyclohexene and cyclooctadiene is distilled off at 80° C. and 0.5 torr and the residue is used for another batch. If required, fresh additional catalyst components are added. Only after three-fold use does the activity of the catalyst diminish, as shown in Table 3.

Table 3

| Ex. | Et$_3$Al$_2$Cl$_3$ mMol | TiCl$_4$ mMol | Dibenzyltoluene g | Reaction temp. °C. | Reaction time min. | Butadiene absorption g |
|---|---|---|---|---|---|---|
| a | 5.4 | 0.9 | 100 | 80 | 60 | 203 |
| b | — | — | — | 80 | 95 | 198 |
| c | 5.4 | — | — | 80 | 75 | 193 |
| d | — | 0.9 | — | 80 | 105 | 288 |

| Ex. | Conversion % | Product Distribution | | | Residue g | Activity g Product / mMoles Ti . h |
|---|---|---|---|---|---|---|
| | | VCH | COD | CDT | | |
| a | 98 | 4.1 | 1.8 | 170.6 | 21.5 | 220 |
| b | 98 | 4.1 | 5.4 | 168.0 | 15.5 | 134 |
| c | 98 | 2.8 | 3.6 | 177.0 | 5.0 | 175 |
| d | 98.5 | 3.9 | 3.4 | 245.7 | 30.0 | 88 |

I claim:

1. In the method for producing cyclododecatri(1,5,9-)enes by catalytically trimerizing butadienes on a catalyst of titanium halide and alkylaluminum halide in the presence of hydrocarbons or halogenated hydrocarbons, the improvement comprising: carrying out the reaction in the presence of dibenzylbenzenes having the general formula:

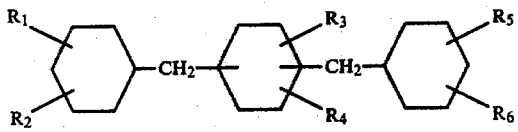

where $R_1$ through $R_6$ represent hydrogen atoms, halogen atoms, alkyl groups, aralkyl groups, cycloalkyl groups or aryl groups, the dibenzylbenzenes being used in at least equimolar amounts with respect to the titanium compound.

2. The method of claim 1, wherein the atomic ratio of aluminum:titanium in said catalyst is between about 2:1 to 140:1.

3. The method of claim 1, wherein the atomic ratio of aluminum:titanium in said catalyst is between about 50:1 to 70:1.

4. The method of claim 3, wherein the catalyst is dissolved in a solvent and said aluminum halide is ethylaluminum sesquichloride, said titanium halide is titanium tetrachloride and said titanium tetrachloride has a concentration of about 0.25 to 5.7 millimoles per liter of said solvent.

5. The method of claim 4, wherein said solvent is said dibenzylbenzenes.

6. The method of claim 1, wherein trimerization is carried out at a temperature of about 20°–100° C.

* * * * *